(12) United States Patent
Mutzel et al.

(10) Patent No.: US 7,960,103 B2
(45) Date of Patent: Jun. 14, 2011

(54) METHOD FOR OBTAINING NEW LIFE FORMS

(75) Inventors: Rupert Mutzel, Berlin (DE); Philippe Marliere, Etiolles (FR); Didier Mazel, Suresnes (FR)

(73) Assignees: Institut Pasteur, Paris (FR); Evologic SA, Evry (FR); Rupert Mutzel, Berlin (DE); Centre National de la Recherche Scientifique, Parix Cedex (FR)

( * ) Notice: Subject to any disclaimer, the term of this patent is extended or adjusted under 35 U.S.C. 154(b) by 944 days.

(21) Appl. No.: 11/519,978

(22) Filed: Sep. 13, 2006

(65) Prior Publication Data

US 2007/0212781 A1    Sep. 13, 2007

Related U.S. Application Data

(63) Continuation of application No. 11/287,349, filed on Nov. 28, 2005, now abandoned, which is a continuation of application No. 11/030,896, filed on Jan. 10, 2005, now abandoned, which is a continuation of application No. 10/482,818, filed as application No. PCT/IB02/03398 on Jul. 8, 2002, now abandoned.

(60) Provisional application No. 60/303,065, filed on Jul. 6, 2001.

(51) Int. Cl.
*C12Q 1/68*    (2006.01)

(52) U.S. Cl. .............................. 435/6; 435/455; 435/383
(58) Field of Classification Search ........................ None
See application file for complete search history.

(56) References Cited

U.S. PATENT DOCUMENTS 5,310,667 A * 5/1994 Eichholtz et al. ............ 435/91.1

FOREIGN PATENT DOCUMENTS

WO          00/34433         6/2000

OTHER PUBLICATIONS

Vulic, Marin, et al., "Mutation, recombination, and incipient speciation of bacteria in the laboratory," Proc. Natl. Acad. Sci., vol. 96, Jun. 1999, pp. 7348-7351.

Mazel, Didier, et al., "Genetic characterization of polypeptide deformylase, a distinctive enzyme of eubacterial translation," The EMBO Journal, vol. 13, No. 4, 1994, pp. 914-923.

* cited by examiner

*Primary Examiner* — James S Ketter
(74) *Attorney, Agent, or Firm* — Oblon, Spivak, McClelland, Maier & Neustadt, L.L.P.

(57) ABSTRACT

The present invention relates to a method for generating a novel form of life comprising the steps consisting of: a) irreversible alteration of the genome of a microbial clone; b) cultivation of a vast population of microbial cells originating from the altered clone obtained in step a) during numerous generations under conditions allowing selection for a higher and stable proliferation rate; c) isolation of descendant clones within the cultivated population of step b) still bearing the alteration of step a).

15 Claims, 4 Drawing Sheets

SEQUENCE LISTING

```
<160> NUMBER OF SEQ ID NOS: 4

<210> SEQ ID NO 1
<211> LENGTH: 169
<212> TYPE: PRT
<213> ORGANISM: Escherichia coli

<400> SEQUENCE: 1

Met Ser Val Leu Gln Val Leu His Ile Pro Asp Glu Arg Leu Arg Lys
1               5                   10                  15

Val Ala Lys Pro Val Glu Glu Val Asn Ala Glu Ile Gln Arg Ile Val
            20                  25                  30

Asp Asp Met Phe Glu Thr Met Tyr Ala Glu Glu Gly Ile Gly Leu Ala
        35                  40                  45

Ala Thr Gln Val Asp Ile His Gln Arg Ile Ile Val Ile Asp Val Ser
    50                  55                  60

Glu Asn Arg Asp Glu Arg Leu Val Leu Ile Asn Pro Glu Leu Leu Glu
65                  70                  75                  80

Lys Ser Gly Glu Thr Gly Ile Glu Glu Gly Cys Leu Ser Ile Pro Glu
                85                  90                  95

Gln Arg Ala Leu Val Pro Arg Ala Glu Lys Val Lys Ile Arg Ala Leu
            100                 105                 110

Asp Arg Asp Gly Lys Pro Phe Glu Leu Glu Ala Asp Gly Leu Leu Ala
        115                 120                 125

Ile Cys Ile Gln His Glu Met Asp His Leu Val Gly Lys Leu Phe Met
```

```
                130                 135                 140
Asp Tyr Leu Ser Pro Leu Lys Gln Gln Arg Ile Arg Gln Lys Val Glu
145                 150                 155                 160

Lys Leu Asp Arg Leu Lys Ala Arg Ala
                165

<210> SEQ ID NO 2
<211> LENGTH: 510
<212> TYPE: DNA
<213> ORGANISM: Escherichia coli

<400> SEQUENCE: 2
atgtcagttt tgcaagtgtt acatattccg gacgagcggc ttcgcaaagt tgctaaaccg      60
gtagaagaag tgaatgcaga aattcagcgt atcgtcgatg atatgttcga cgatgtgtac     120
gcagaagaag gtattggcct ggcggcaacc caggttgata tccatcaacg tatcattgtt     180
attgatgttt cggaaaaccg tgacgaacgg ctagtgttaa tcaatccaga gcttttagaa     240
aaaagcggcg aaacaggcat tgaagaaggt tgcctgtcga tccctgaaca acgtgcttta     300
gtgccgcgcg cagagaaagt taaaattcgc gcccttgacc gcgacggtaa accatttgaa     360
ctggaagcag acggtctgtt agccatctgt attcagcatg agatggatca cctggtcggc     420
aaactgttta tggattatct gtcaccgctg aacaacaac gtattcgtca gaaagttgaa     480
aaactggatc gtctgaaagc ccgggcttaa                                      510

<210> SEQ ID NO 3
<211> LENGTH: 315
<212> TYPE: PRT
<213> ORGANISM: Escherichia coli

<400> SEQUENCE: 3

Met Ser Glu Ser Leu Arg Ile Ile Phe Ala Gly Thr Pro Asp Phe Ala
1               5                   10                  15

Ala Arg His Leu Asp Ala Leu Leu Ser Ser Gly His Asn Val Val Gly
                20                  25                  30

Val Phe Thr Gln Pro Asp Arg Pro Ala Gly Arg Gly Lys Lys Leu Met
            35                  40                  45

Pro Ser Pro Val Lys Val Leu Ala Glu Glu Lys Gly Leu Pro Val Phe
        50                  55                  60

Gln Pro Val Ser Leu Arg Pro Gln Glu Asn Gln Gln Leu Val Ala Glu
65                  70                  75                  80

Leu Gln Ala Asp Val Met Val Val Val Ala Tyr Gly Leu Ile Leu Pro
                85                  90                  95

Lys Ala Val Leu Glu Met Pro Arg Leu Gly Cys Ile Asn Val His Gly
                100                 105                 110

Ser Leu Leu Pro Arg Trp Arg Gly Ala Ala Pro Ile Gln Arg Ser Leu
            115                 120                 125

Trp Ala Gly Asp Ala Glu Thr Gly Val Thr Ile Met Gln Met Asp Val
130                 135                 140

Gly Leu Asp Thr Gly Asp Met Leu Tyr Lys Leu Ser Cys Pro Ile Thr
145                 150                 155                 160

Ala Glu Asp Thr Ser Gly Thr Leu Tyr Asp Lys Leu Ala Glu Leu Gly
                165                 170                 175

Pro Gln Gly Leu Ile Thr Thr Leu Lys Gln Leu Ala Asp Gly Thr Ala
            180                 185                 190

Lys Pro Glu Val Gln Asp Glu Thr Leu Val Thr Tyr Ala Glu Lys Leu
        195                 200                 205
```

```
Ser Lys Glu Glu Ala Arg Ile Asp Trp Ser Leu Ser Ala Ala Gln Leu
    210                 215                 220

Glu Arg Cys Ile Arg Ala Phe Asn Pro Trp Pro Met Ser Trp Leu Glu
225                 230                 235                 240

Ile Glu Gly Gln Pro Val Lys Val Trp Lys Ala Ser Val Ile Asp Thr
                245                 250                 255

Ala Thr Asn Ala Ala Pro Gly Thr Ile Leu Glu Ala Asn Lys Gln Gly
            260                 265                 270

Ile Gln Val Ala Thr Gly Asp Gly Ile Leu Asn Leu Leu Ser Leu Gln
        275                 280                 285

Pro Ala Gly Lys Lys Ala Met Ser Ala Gln Asp Leu Leu Asn Ser Arg
    290                 295                 300

Arg Glu Trp Phe Val Pro Gly Asn Arg Leu Val
305                 310                 315

<210> SEQ ID NO 4
<211> LENGTH: 948
<212> TYPE: DNA
<213> ORGANISM: Escherichia coli

<400> SEQUENCE: 4
gtgtcagaat cactacgtat tattttttgcg ggtacacctg actttgcagc gcgtcatctc      60
gacgcgctgt tgtcttctgg tcataacgtc gttggcgtgt tcacccagcc agaccgaccg     120
gcaggacgcg gtaaaaaact gatgcccagc ccggttaaag ttctggctga ggaaaaaggt     180
ctgcccgttt ttcaacctgt ttccctgcgt ccacaagaaa accagcaact ggtcgccgaa     240
ctgcaggctg atgttatggt cgtcgtcgcc tatggtttaa ttctgccgaa agcagtgctg     300
gagatgccgc gtcttggctg tatcaacgtt catggttcac tgctgccacg ctggcgcggt     360
gctgcaccaa tccaacgctc actatggggcg ggtgatgcag aaactggtgt gaccattatg     420
caaatggatg tcggtttaga caccggtgat atgctctata agctctcctg cccgattact     480
gcagaagata ccagtggtac gctgtacgac aagctggcag agcttggccc acaagggctt     540
atcaccacgt tgaaacaact ggcagacggc acggcgaaac cagaagttca ggacgaaact     600
cttgtcactt acgccgagaa gttgagtaaa gaagaagcgc gtattgactg gtcactttcg     660
gcagcacagc ttgaacgctg cattcgcgct ttcaatccat ggccaatgag ctggctggaa     720
attgaaggac agccggttaa agtctggaaa gcatcggtca ttgatacggc aaccaacgct     780
gcaccaggaa cgatccttga agccaacaaa caaggcattc aggttgcgac tggtgatggc     840
atcctgaacc tgctctcgtt acaacctgcg ggtaagaaag cgatgagcgc gcaagacctc     900
ctgaactctc gtcgggaatg gtttgttccg ggcaaccgtc tggtctga                  948
```

METHOD FOR OBTAINING NEW LIFE FORMS

The present invention relates to a method for generating a novel form of life comprising the steps consisting of:
a) irreversible alteration of the genome of a microbial clone;
b) cultivation of a vast population of microbial cells originating from the altered clone obtained in step a) during numerous generations under conditions allowing selection for a higher and stable proliferation rate;
c) isolation of descendant clones within the cultivated population of step b) still bearing the alteration of step a).

The invention is particularly useful for production of recombinant proteins in bacteria, more particularly in eubacterial hosts. A eubacterial host defective in the genes for Met-tRNAi transformylase and polypeptide deformylase is described which grows in minimal and complex nutrient media at 30° C., 37° C. and 42° C. with near wild-type rate. In this eubacterium protein synthesis does not require N-formyl methionine as the initiator methionine, protein synthesis instead is initiated with unmodified methionine. The absence of peptides which retain N-formyl methionine in this eubacterium makes it particularly suited for the expression of recombinant proteins for pharmaceutical use.

BACKGROUND

Many attempts to drastically modify bacteria for use in industry have failed since such modifications are most of the time lethal or lead to uncompetitive and unstable organisms.

For example; in eubacteria, peptide synthesis is initiated at methionine start codons which are read by N-formyl methionine TRNA. Prior to translation initiation the methionyl moiety of the charged tRNA is N-formylated by the action of Met-tRNAi transformylase. The N-formyl group is removed from the native protein by polypeptide deformylase (E.C. 3.5.1.27), and the initiator methionine can then be cleaved off by methionine aminopeptidase, completing the primer methionine cycle. In contrast, archaea and eukaryotes have a primer methionine cycle devoid of N-formylating and deformylating activities (for review see Mazel et al., 1994, 1996).

Expression of eukaryotic proteins in eubacterial hosts often results in the production of recombinant proteins that retain an N-terminal formylmethionyl residue (examples include bovine somatotropin [Bogosian et al., 1989]; eel growth hormone [Sugimoto et al., 1990]; human granulocyte colony-stimulating factor [Clogston et al., 1992]; bovine fatty acid-binding protein [Specht, et al., 1994]; bovine cytochrome P450 [Dong et al. 1995]; Methanothermus fervidus histone A [Sandman et al., 1995]; human interleukin-5 [Rose et al., 1992]; human parathyroid hormone [Rabbani et al., 1988; Hogset et al., 1990]; human gamma-interferon [Honda et al., 1989]). In addition retention of N-formyl methionine has been found in endogeneous E. coli proteins (Hauschild-Rogat, 1968; Marasco et al., 1984; Milligan and Koshland, 1990).

Since N-formylated peptides are a major indicator of eubacterial infections for the mammalian immune system and are highly immunogenic, incomplete deformylation precludes, for example, the use of N-formylated preparations for therapeutic purposes.

Several approaches to circumvent this problem have been proposed, e.g., expression in the presence of trimethoprim and thymidine (Sandman et al., 1995), overexpression of peptide deformylase in the host (U.S. Pat. No. 6,190,902), expression as a protein fusion either with an N-terminal peptide that can be removed in vitro by a specific protease or with an N-terminal leader peptide which is cleaved during transport of the nascent protein in a non-cytoplasmatic compartment. Finally, the N-formyl group may also be removed by mild acid hydrolysis, or the fraction of the protein retaining N-formyl methionine may be separated from the correctly processed protein by purification procedures.

Each of these approaches has significant disadvantages. Addition of trimethoprim and thymidine is costly, requires manipulation of the culture that will express the recombinant protein, and may slow down growth of the host. Overexpression of peptide deformylase requires a stable plasmid construct. in the host that has to be selected for; moreover, deformylation may be less than 100% effective. Expression of fusion proteins requires exact molecular constructions; chemical hydrolysis with acid may cause damage to the rest of the protein. Finally, none of these approaches guarantees a final preparation that is absolutely free of N-formylated peptides derived either from the recombinant protein or from contaminations with endogenous host peptides.

The above mentioned drawbacks are solved if one could produce peptides in bacteria that are freed of the N-transformylation system. But, for bacteria that have evolved with this system for billions of year, removal of this system would normally result in death or serious impairment ultimately leading to organisms that are uncompetitive and genetically unstable. Indeed, when these modified bacteria are in contact with non modified bacteria they either recuperate the lost functional genetic elements or they simply disappear in favor of the more competitive natural bacteria.

One could also think that it would take billions of years of evolution to see emergence of bacteria devoid of the N-transformylation activity.

In connection with the invention, the N-transformylation system have been inactivated in bacteria having normally the N-transformylation system. Following a selective process, strains that are genetically stable and capable of competing with the natural bacteria have been obtained in only one month.

The invention opens new possibilities for obtaining new organisms that will constitute new species useful in all kind of industries by means of resurgent evolution.

DESCRIPTION

Therefore, in a first embodiment the invention relates to a method for conducting resurgent evolution of microbial strains comprising the steps consisting of:
a) irreversible alteration of the genome of a microbial clone;
b) cultivation of a vast population of a microbial clone as obtained in step a) during numerous generations under conditions allowing selection of accelerated proliferation not limited by the nutritional supply;
c) isolation of descendant clones within the cultivated population of step b) on the basis of increased proliferation rate during, said clones having enhanced metabolic activities compared to the microbial clones of step a) while still bearing the alteration of step a).

In this method, microbial strains can be bacteria such as E. Coli.

Steps b) and c) essentially consist of resurgent evolution, which means that the rate of proliferation of bacteria obtained after culturing during a prolonged period of time (about 1 month for E. Coli) is significantly increased compared to bacteria of step a).

For example, the rate of proliferation of bacteria obtained after resurgent evolution in step c) can be comparable to rate of proliferation of the natural bacteria.

This resurgence is the result of the acquisition of a succession of mutations which stabilized the evolution to reach a new specie or to break off with the philogenic branch of the natural bacteria.

In a particular embodiment, the new specie is capable of competing with the natural bacteria. In this regards, the new specie is genetically stable even in presence of the natural bacteria, which means that the bacteria obtained after completion of the method cannot revert to the phenotype and genotype of the natural (initial) bacteria. In other words the new specie is stable in that it cannot genetically revert to the natural bacteria.

The new specie can be for example a humanized bacteria.

The successive mutations acquired by the bacteria of the new specie constitute tags that are genetically stable and form a particular branding for such new specie. The branding can originates from the metabolic modifications acquired during steps b) and c).

Step c) can be performed in minimal medium at 37° C. or more, an important feature being that there is unlimited supply of nutriments.

In addition, the isolation in step c) can be performed when the bacteria of step b) reach a plateau in the rate of proliferation. By repeating these steps, several maximum proliferation rates can be reached successively until the isolated clones display a rate which is satisfactory, for example a rate which is comparable to the natural bacteria.

In a specific embodiment, the alteration is the inactivation of at least one gene in step a). The inactivation can be a deletion, a mutation, or a substitution with other sequences from other organisms.

The gene can be the fmt gene coding for the Met-tRNAi transformylase. In this case, step a) can comprise the deletion of the entire def-fmt operon. As mentioned above, the natural bacteria can be *E. Coli*.

Therefore, in this case, the bacteria of step c) is devoid of N-formylating activities.

The invention is also directed to a method as defined above, wherein steps b) and c) are performed with a device comprising:
a) at least a first and at least a second culture vessel (4,6) for receiving a culture (38);
b) a gas source (12);
c) a medium source (18);
d) a source (20) for a sterilizing agent (21); and
e) a conduit system with means for selectively connecting one of said two culture system (4 or 6) with said medium source (18) as well as said two culture vesssels (4, 6) with each other and for selectively connecting said respective other culture vessel (4 or 6) with said source (20) for said sterilizing agent (21).

This device and the above numbers are fully explicated in WO 00/34433, more particularly in FIG. 1 which is incorporated by reference in the description.

In another embodiment, the invention is aimed at a mutated bacteria obtainable by the method defined above, wherein said bacteria constitutes a new specie that can not genetically revert to the natural bacteria.

In another embodiment, the invention is aimed at a mutated bacteria obtainable by the method defined above, wherein said bacteria belongs a phylogenic class which differs from the natural bacteria.

Such mutated bacteria can compete with the natural bacteria in term of proliferation rate. It comprises several acquired mutations constituting tags leading to a new branding, said mutations being genetically stable even in presence of the natural bacteria.

The invention relates to a microbial strain comprising an irreversible alteration of its genome, while displaying an increased proliferation rate compared to the non-altered bacteria. In addition, this microbial strain can have enhanced metabolic activities or a different information treatment process.

The invention is also directed to a mutated bacteria which has been modified by the inactivation of at least one gene, wherein said bacteria have acquired mutations during provoked resurgent evolution leading to a genetically stable new specie. The acquired mutations are stable and constitute tags leading to a new branding.

More particularly, the invention relates to a mutated bacteria comprising an inactivated Met-tRNA transformylase, wherein said bacteria acquired mutations during provoked resurgent evolution leading to a genetically stable new specie. Said bacteria does not produce formyl-met peptides and is capable of competing with the natural bacteria in terms of proliferation rate.

The invention is aimed at a mutated bacteria consisting of strain β2137 deposited at the CNCM on Jul. 26, 2001 (Collection Nationale de Cultures de Microorganismes, Institut Pasteur, 28 rue du Docteur Roux, 75724 Paris cedex 15, France) under the accession number I-2707.

The above bacteria of the invention can be transformed with a vector comprising the coding sequence for a peptide or protein of interest. More particularly, they are non formylated peptides or proteins.

As mentioned above, the present invention contemplates a mutated bacteria comprising an inactivated Met-tRNA transformylase, wherein said bacteria acquired mutations during provoked resurgent evolution leading to a genetically stable new specie.

This bacteria is an *E. coli* strain with a primer methionine cycle similar to that in eucaryotic cells. This strain does non longer harbor the def-fmt operon encoding Met-tRNAi transformylase and polypeptide deformylase and thus can not N-formylate Met-tRNAi. Removal of N-formyl groups from expressed proteins by any of the techniques described above is thus no longer required.

The fmt and def genes from *E. coli* were previously isolated (Guillon et al., 1992; Mazel et al., 1994) and shown to be highly conserved among eubacteria (Mazel et al., ). Deletion mutants for either the fmt gene (Guillon et al., 1992) or the entire def-fmt operon (Mazel et al., 1994, D[def-fmt]) were created. The resulting mutants were reported to be severely impaired in growth. The fmt mutant has an 8.61-fold decreased growth rate at 37° C. in rich medium and does not grow at 42° C. (Guillon et al., 1992). The def-fmt mutant has a similarly decreased growth rate in minimal medium at 37° C., and growth is completely impaired in this medium at 42° C. ( ). Whereas deletion of the fmt gene alone leaves the mutant bacteria viable, deletion of the def gene alone as well as re-introduction of the fmt gene into a def-fmt background is lethal (Mazel et al., 1994), demonstrating that essential bacterial proteins either have to be deformylated, and/or that the initiator methionine has to be cleaved off in order to render these proteins functional.

For the purpose of the present invention, a def-fmt deletion mutant was selected for enhanced growth rates under permanent proliferation in minimal medium at 37° C. until its growth rate approximated that of the parent wild-type bacterium.

Therefore, the invention is aimed at bacteria such as a eubacterium with altered translational mechanism such that it contains no fmt and def genes yet grows at wt rate. Said *E. coli* formyl-free strain is growing at temperatures higher than 37° C. and can be used for the expression of recombinant proteins and peptides which are not contaminated with N-formylated peptides.

The invention also relates to a method for provoking resurgent evolution of bacteria in which at least one gene has been inactivated comprising the steps consisting of:
a) culturing said mutated bacteria in suspension in continuous proliferation state and constant cell density;
b) selecting of a subpopulation of bacteria on the basis of increased-proliferation rate after a prolonged period of time during which said subpopulation acquired mutations resulting in a resurging evolution; said mutated bacteria still bearing the initial mutation.

The initial mutation can consist of the inactivation of at least one gene or of part of all of an operon. The resurgent evolution allows the acquisition of successive mutations leading to a new genetically stable specie adapted to natural or artificial environments.

The invention also relates to a method for generating stable bacterial strains with modified information transfer process comprising the steps consisting of:
a) irreversible alteration of the genome of a microbial clone;
b) cultivation of a vast population of microbial cells originating from the altered clone obtained in step a) during numerous generations under conditions allowing selection for a higher and stable proliferation rate;
c) isolation of descendant clones within the cultivated population of step b) still bearing the alteration of step a).

The term "modified information transfer" may refer to a non natural information treatment process ultimately leading to a novel form of life.

The invention also relates to a method for conducting microbial evolution leading to a change in the phylogenic classification comprising the steps consisting of:
a) irreversible alteration of the genome of a microbial clone;
b) cultivation of a vast population of microbial cells originating from the altered clone obtained in step a) during numerous generations under conditions allowing selection for a higher and stable proliferation rate;
c) isolation of descendant clones within the cultivated population of step b) still bearing the alteration of step a).

The invention also relates to a method for generating a novel form of life comprising the steps consisting of:
a) irreversible alteration of the genome of a microbial clone;
b) cultivation of a vast population of microbial cells originating from the altered clone obtained in step a) during numerous generations under conditions allowing selection for a higher and stable proliferation rate;
c) isolation of descendant clones within the cultivated population of step b) still bearing the alteration of step a).

In the above methods, step b) can consist of the cultivation of a vast population of a microbial clone as obtained in step a) during numerous generations under conditions allowing selection of accelerated proliferation not limited by the nutritional supply; And step c) can consist of the isolation of descendant clones within the cultivated population of step b) on the basis of increased proliferation rate during, said clones having enhanced metabolic activities compared to the microbial clones of step a) while still bearing the alteration of step a).

BRIEF DESCRIPTION OF THE DRAWINGS

FIG. 1: The primer methionine cycle in eubacteria (FIG. 1*a*) and archaea and eukaryotes (FIG. 1*b*) metg, met-tRNA synthetase; fmt, met-tRNAi transformylase; def, polypeptide deformylase; map, methionine amino peptidase; aa, amino acid; f, formyl: pp, polypeptide. Modified after (3).

EXAMPLE 1

Selection of Enhanced Growth Rate in the Def-fmt Mutant

I—Materials and Methods 1.1 Strains
γ2045
Our reference strain is γ2045
*Escherichia coli* MG1655 Δ(def-fmt)::cat, dnaQ::miniTn10 [$Cm^R$, $Tc^R$]

MG 1655 is a wild-type K12 strain of *E. coli* (see EMBO J. (1994) 13:914-923) Δ(def-fmt) means deletion of the def-fmt operon, which encodes the polypeptide deformylase and the Met-tRNAi transformylase activities. This allele has been described (EMBO J. (1994) 13:914-923).

The writing ::cat means the insertion of a cat (chloramphenicol acetyl-transferase) gene in the Δ(def-fit) locus.

dnaQ::miniTn10 means that the dnaQ gene (epsilon subunit of the DNA polymerase, the proof-reading subunit) is interrupted by the insertion of a minitransposon Tn10 which confers the tetracycline resistance

[CmR, TcR] means that the strain is resistant to chloramphenicol (25 micg/ml) and to Tetracycline (15 micg/ml).

This bacterial strain carries a deletion of the def-fmt operon and is consequently defective in the Met-tRNAi transformylase and polypeptide deformylase activities. This strain also carries dnaQ mutation and consequently shows a mutator phenotype. This strain is a derivative of β2124 that has been selected to grow in minimal and complex nutrient media at 30° C., 37° C. and 42° C. with near wild-type rate (approximately 25 min in LB and approximately 80 min in MS minimal medium (Richaud (1993), J. Biol. Chem. 268:26827-26835) with mannitol as carbon source at final concentration 0.2% at 37° C.). The original β2124 strain shows a growth rate of approximately 200 min in MS minimal medium+mannitol at 37° C. γ2045, the β2124 derivative, was selected for enhanced growth rates under permanent proliferation in minimal medium at 37° C. until its growth rate reached that of MG1655, the parent wild-type bacterium.

The mutator phenotype can be rescued by complementation with a dnaQ wild type allele expressed either from a plasmid or from the chromosome, through an allele replacement in γ2045.

β2137

Our reference strain is β2137:

*Escherichia coli* MG1655, Δfmt::cat [44° C.$^S$, Cm$^R$]

MG1655 is a wild-type K12 strain of *E. coli* (see EMBO J. (1994) 13:914-923) Δfmt means deletion of the fmt gene which encodes the Met-tRNAi transformylase activity. This allele has never been described, it is a Pst I deletion, internal to fmt (nucleotides 247 to 484).

The writing::cat means the insertion of a cat (chloramphenicol acetyl-transferase) gene at the PstI site of the deletion. The cat gene is identical to the one used for the construction of the Δ(def-fmt)::cat allele (see EMBO J. (1994) 13:914-923). [44° C.$^S$, Cm$^R$] means that the strain is thermosensitive and resistant to chloramphenicol (25 micg/ml).

This bacterial strain carries a deletion of the fmt gene and is consequently defective in the Met-tRNAi transformylase activity. This strain is a derivative of MG 1655 that has a growth rate of approximately 200 min in MS minimal medium+mannitol at 37° C.

DATA:
DEF (SEQ ID N° 1):
MSVLQVLHIPDERLRKVAKPVEEVNAEIQRIVDDMFETMYAEEGIGLAAT

QVDIHQRIIVIDVSENRDERLVLINPELLEKSGETGIEEGCLSIPEQRAL

VPRAEKVKIRALDRDGKPFELEADGLLAICIQHEMDHLVGKLFMDYLSPL

KQQRIRQKVEKLDRLKARA def (gene) (SEQ ID N° 2):
atgtcagttttgcaagtgttacatattccggacgagcggcttcgcaaagt tgctaaaccggtagaagaagtgaatgcagaaattcagcgtatcgtcgatg atatgttcgagacgatgtacgcagaagaaggtattggcctggcggcaacc caggttgatatccatcaacgtatcattgttattgatgtttcggaaaaccg tgacgaacggctagtgttaatcaatccagagcttttagaaaaaagcggcg aaacaggcattgaagaaggttgcctgtcgatccctgaacaacgtgcttta gtgccgcgcgcagagaaagttaaaattcgcgcccttgaccgcgacggtaa accatttgaactggaagcagacggtctgttagccatctgtattcagcatg agatggatcacctggtcggcaaactgtttatggattatctgtcaccgctg aaacaacaacgtattcgtcagaaagttgaaaaactggatcgtctgaaagc ccgggcttaa

FMT (SEQ ID N° 3):
MSESLRIIFAGTPDFAARHLDALLSSGHNVVGVFTQPDRPAGRGKKLMPS

PVKVLAEEKGLPVFQPVSLRPQENQQLVAELQADVMVVVAYGLILPKAVL

EMPRLGCINVHGSLLPRWRGAAPIQRSLWAGDAETGVTIMQMDVGLDTGD

MLYKLSCPITAEDTSGTLYDKLAELGPQGLITTLKQLADGTAKPEVQDET

LVTYAEKLSKEEARIDWSLSAAQLERCIRAFNPWPMSWLEIEGQPVKVWK

ASVIDTATNAAPGTILEANKQGIQVATGDGILNLLSLQPAGKKAMSAQDL

LNSRREWFVPGNRLV fmt (gene) (SEQ ID N° 4):
gtgtcagaatcactacgtattattttttgcgggtacacctgactttgcagc gcgtcatctcgacgcgctgttgtcttctggtcataacgtcgttggcgtgt tcacccagccagaccgaccggcaggacgcggtaaaaaactgatgcccagc ccggttaaagttctggctgaggaaaaaggtctgcccgttttttcaacctgt ttccctgcgtccacaagaaaaccagcaactggtcgccgaactgcaggctg atgttatggtcgtcgtcgcctatggtttaattctgccgaaagcagtgctg gagatgccgcgtcttggctgtatcaacgttcatggttcactgctgccacg ctggcgcggtgctgcaccaatccaacgctcactatgggcgggtgatgcag aaactggtgtgaccattatgcaaatggatgtcggtttagacaccggtgat atgctctataagctctcctgcccgattactgcagaagataccagtggtac gctgtacgacaagctggcagagcttggcccacaagggcttatcaccacgt tgaaacaactggcagacggcacggcgaaaccagaagttcaggacgaaact cttgtcacttacgccgagaagttgagtaaagaagaagcgcgtattgactg gtcactttcggcagcacagcttgaacgctgcattcgcgctttcaatccat ggccaatgagctggctggaaattgaaggacagccggttaaagtctggaaa gcatcggtcattgatacggcaaccaacgctgcaccaggaacgatccttga agccaacaaacaaggcattcaggttgcgactggtgatggcatcctgaacc tgctctcgttacaacctgcgggtaagaaagcgatgagcgcgcaagacctc ctgaactctcgtcgggaatggtttgttccgggcaaccgtctggtctga 1.2 Media Strains were cultivated in minimal medium (4 mM citrate× $H_2O$, 1 mM $MgSO_4$×7 $H_2O$, 10 mM $NH_4Cl$, 0.2% w/v mannitol and 1 ml/l NTA-trace elements*) at 37° C. Solid media contained 1.8% agar.

(*NTA-trace elements×1000)

| Component | Concentration (M) |
| --- | --- |
| Nitrilotriacetic acid | $10^{-2}$ |
| $CaCl_2$ × $2H_2O$ | $3 \times 10^{-3}$ |
| $FeCl_3$ × $6H_2O$ | $2 \times 10^{-3}$ |
| $MnCl_2$ × $4H_2O$ | $10^{-3}$ |
| $ZnCl_2$ | $10^{-3}$ |
| $H_3BO_3$ | $3 \times 10^{-4}$ |
| $CrCl_3$ × $6H_2O$ | $3 \times 10^{-4}$ |
| $CoCl_2$ × $6H_2O$ | $3 \times 10^{-4}$ |
| $CuCl_2$ × $2H_2O$ | $3 \times 10^{-4}$ |
| $NiCl_2$ × $6H_2O$ | $3 \times 10^{-4}$ |
| $Na_2MoO_4$ × $2H_2O$ | $3 \times 10^{-4}$ |
| $Na_2SeO_3$ × $5H_2O$ | $3 \times 10^{-4}$ |

1.3 Continuous cultivation

Populations of *E. coli* β2124 or β2116 were kept under contiuous proliferation at 37° C. in the device described by Mutzel and Marlière in WO 00/34433.

Culture volume was 26.0 ml. A turbidostat regime was applied, keeping the $OD_{600\,nm}$ of the culture at ca. 1.0. Growth rates calculated from the culture volume (V) and the flow of fresh medium (W) according to R=W/V 1/ln2 were averaged over 24 h periods. Calculated growth rates were compared with growth rates obtained from batch cultures.

Stocks were prepared by mixing 0.1 ml DMSO with 1 ml samples withdrawn from the device and kept at −70° C.

II—Results

An *E. coli* Strain for Expression of N-Formyl-Free Polypeptides

Figure 1A:
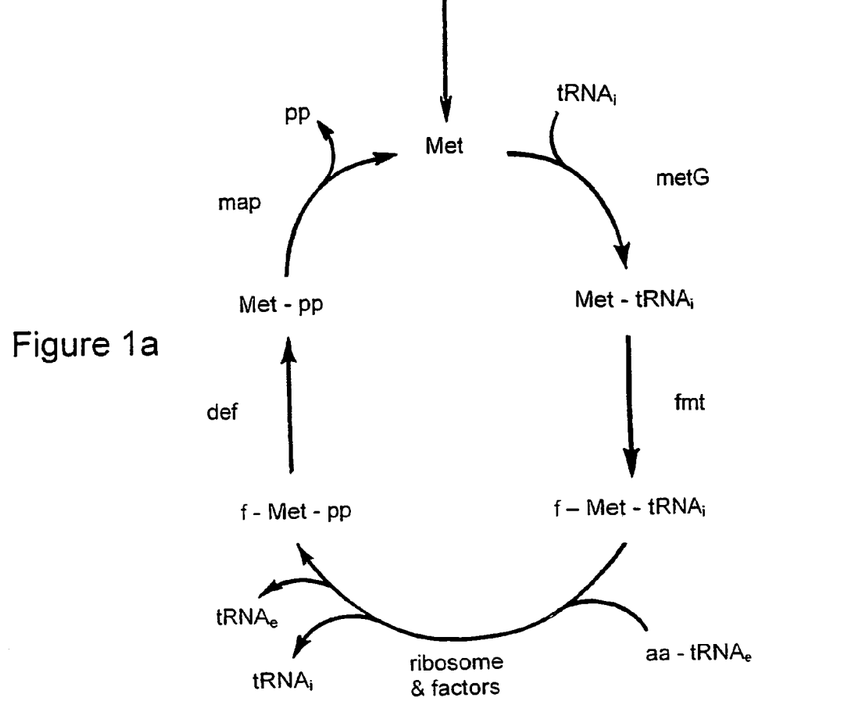
Figure 1B:
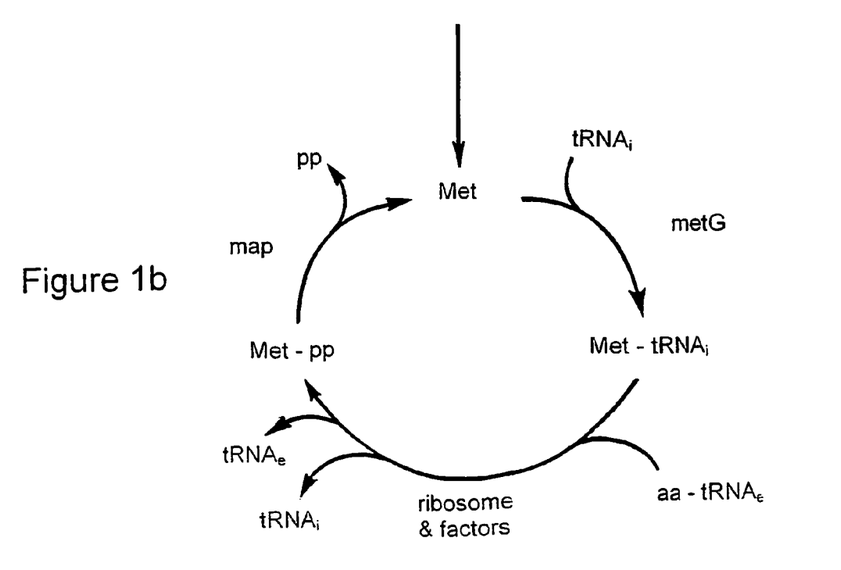

In eubacteria peptide synthesis is initiated at methionine start codons which are read by N-formyl methionine tRNA. Prior to translation initiation, the methionyl moiety of the charged tRNA is N-formylated by the action of Met-tRNAi transformylase. The N-formyl group is removed from the native protein by polypeptide deformylase, and the initiator methionine can then be cleaved off by methionine aminopeptidase, completing the primer methionine cycle (FIG. 1*a*). In contrast, archaea and eukaryotes have a primer methionine cycle devoid of N-formylating and deformylating activities (FIG. 1*b*).

Expression of eukaryotic proteins in eubacterial hosts often results in the production of recombinant proteins that retain an N-terminal formylmethionyl residue. Since N-formylated peptides are highly immunogenic, incomplete deformylation precludes, for example, their use for therapeutic purposes. Several approaches to circumvent this problem have been proposed. e.g., expression in the presence of trimethoprim and thymidine (Sandman, K., Gryling. R. A. and Revve, J. N. (1995): Improved N-terminal processing of recombinant proteins synthesized in *E. coli*. Biotechnology 13, 504-506) or overexpression of peptide deformylase in the host (Warren, W. C., Bentle, K. A. Schlittler, M. R., Schwane, A. C., O'Neil, J. P. and Bogosian, G. (1996): Increased production of peptide deformylase eliminates retention of formylmethionine in bovine somatotropin overproduced in *E. coli*. Gene 174, 235-238).

The inventors have opted for a radical solution, simplifying the primer methionine cycle in *E. coli* by deletion of the def-fmt operon that encodes polypeptide deformylase and met-tRNAi transformylase, and improving the resulting, crippled strain by selecting for increasing growth rates (and therefore improved rates of protein synthesis) under permanent proliferation in suspension.

The inventors have isolated the def and fmt genes from *E. coli* and created a deletion mutant (D[def-fmt]) devoid of both genes (Mazel, D., Pochet, S. and Marlière, P. (1994): Genetic characterization of polypeptide deformylase a distinctive enzyme of eubacterial translation. EMBO J. 13, 914-923). The resulting strain was found to be viable, however its growth rate was dramatically reduced, from 0.9 per h to 0.25 per h in minimal medium at 37° C.

Protein synthesis in living cells is dependent on the concerted action of a complex assembly of the protein and rRNA constituents of ribosomes and a host of factors catalyzing aminoacylation of tRNAs, initiation, elongation and termination of translation as well as maturation of nascent polypeptides. N-terminal formylation is among the most conserved features that distinguish eubacteria from archaea and eukaryotes. Removing the enzymes that catalyze the corresponding reactions is therefore expected to remove the efficiency of protein synthesis far from its wild-type optimum. Evolutionary resurrection from this type of genetic injury will require multiple adaptive mutations to render the bacterial translation machinery more similar to that found in eukaryotes. State-of-the-art technologies for directed evolution ex vivo are unable to predict and select the adaptive mutations that would re-establish wild-type protein synthesis rates in a D(def-fmt) background.

Figure 2:
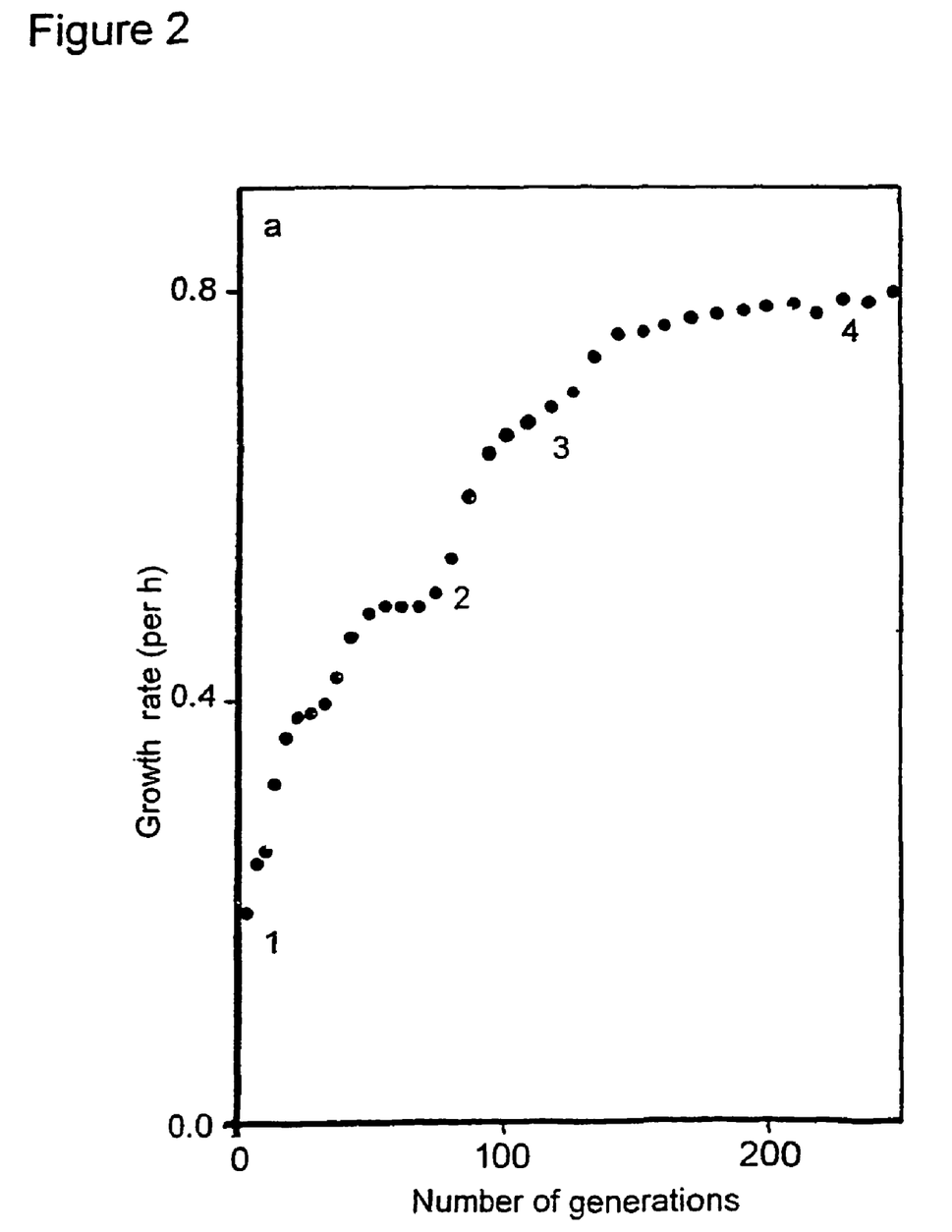
FIG. 2: In vivo evolution of a D(def-fmt) mutant under permanent proliferation. a, Cells were kept under permanent proliferation in minimal medium at 37° C. A turbidostat regime at $5\times10^8$ cells/ml was applied. Growth rates are averaged over 24 h periods. Two independent runs are shown. b, Input (1) and evolved strains isolated during the process (2, 3, 4; c.f., numbers and open circles in a) were grown on minimal agar for 36 h at 37° C.

In vivo evolution of the D(def-fmt) mutant under permanent proliferation in suspension in a turbidostat regime yields variants with increasing growth rate, approximating wild-type growth rate after about 1 month (ca. 300 generations) of permanent selection (FIG. 2). We observed a drastically increases biomass production of evolved derivatives tested for growth on minimal agar as compared to the input D(def-fmt) mutant. Stepwise increases in the growth rate of the evolving population result in selection and fixation of successive adaptive mutations.

We have evidence that the protein met-tRNA synthetase, certain ribosomal proteins, initiation factor 2. and methionine aminopeptidase are altered in the output strains.

Figure 3:
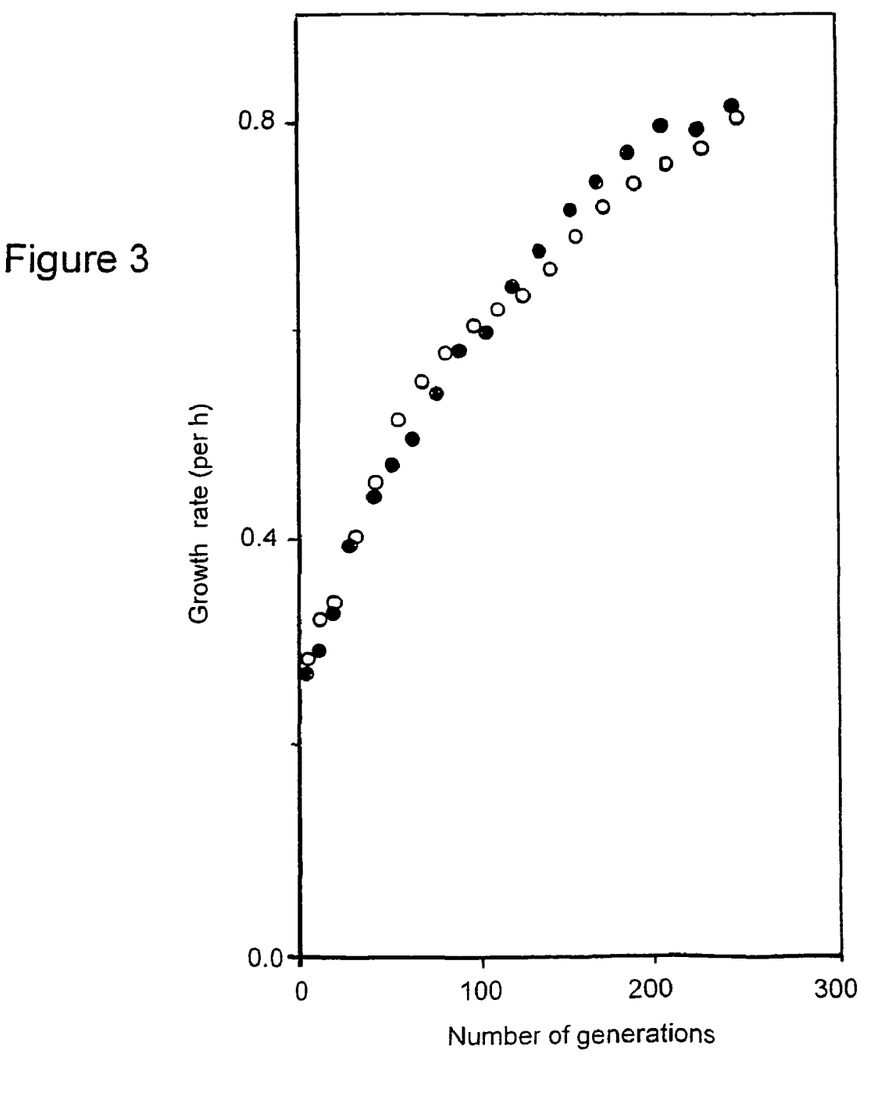
FIG. 3: In vivo evolution of a D(def-fmt) mutant at increased mutation rates. Two independent runs are shown.
Figure 4:
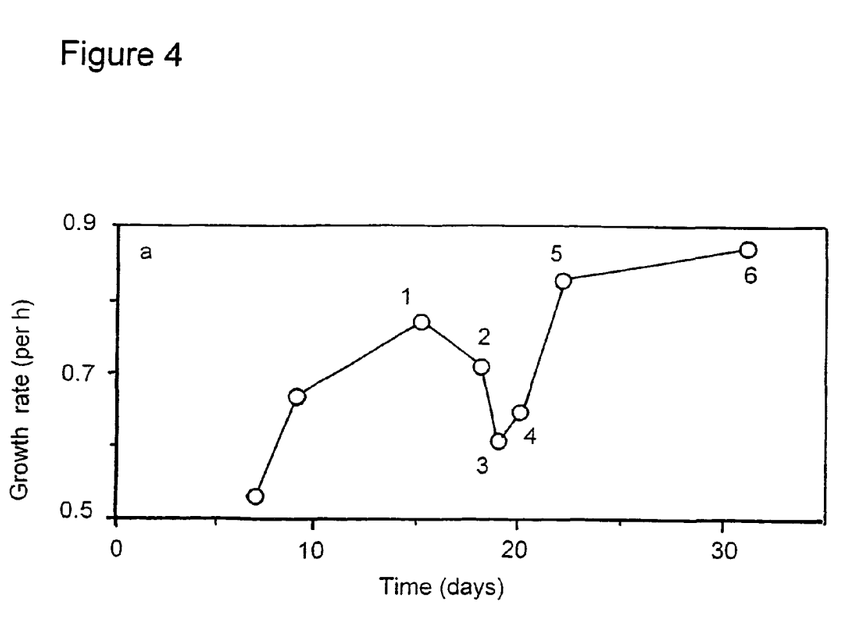
FIG. 4: Emergence and selection of adhesive variants in a conventional turbidostat, and counter-selection of adhesive variants by the device described in WO 00/34433. Starting at point 1, adhesive variants were allowed to compete with cells in suspension periodic destruction of static variants was re-established at point 3; a, Growth rates of the populations as measured in batch culture. b. Adhesion of cell material to glass surfaces. Isolates (points 1-6 in a) were cultivated in glass tubes for 20 h at 37° C. Arrowheads point to material that accumulated on the surface during cultivation.

The evolutionary process can be accelerated by increasing variation in the population (FIG. 3). When mutation rates in the population under selection were increased by a factor of about 1.000, wild-type growth rates were approximated within about half the time required for the process shown in FIG. 2.

Current technology for continuous proliferation of cells in suspension suffers a major drawback, selection of adhesive variants which stick to inner surfaces of the device and escape the selective pressure imposed by continuous or conditional dilution (Chao, L. and Ramsdell, G. (1985): The effects of wall populations on coexistence of bacteria in the liquid phase of chemostat cultures. J. Gen. Microbiol. 131, 1229-1236). In principle, this can be avoided by serial subculture of cells in suspension (Lenski, R. E. and Travisano, M. (1994):Dynamics of adaptation and diversification: A 10,àáà-generation experiment with bacterial populations. Proc. Natl. Acad. Sci. USA 91, 6808-6814), a technique where cells in suspension are frequently transferred into fresh culture vessels (i.e., surfaces are periodically discarded), creating a selective disadvantage for static variants. At an industrial scale, serial subculture technology has not been systematically exploited because it is laborious and requires absolute sterility during transfers.

Automated technology for the permanent proliferation of populations of cells exclusively in suspension has been proposed in WO 00/34433. During the course of an experiment similar to that shown in FIG. 3, operation of the device was manipulated such that static, adhesive variants were no longer destroyed and could freely compete with cells in suspension. Highly adhesive variants accumulated rapidly (data not shown). In parallel, the growth rate of the population decreased, demonstrating that these static variants are not subject to the selective pressure imposed on the cells in suspension. When proper operation of the device was re-established, these variants were rapidly and effectively eliminated from the evolving population.

CONCLUSION

The automated device described in WO 00/34433 is the first operational apparatus which allows permanent proliferation of living cells under defined, selective conditions and is particularly suited for the resurgent evolution of mutated bacteria.

The automated process frequently and effectively destroys static variants in any part of the device, overcoming the primary obstacle to continuous proliferation of cells in suspension for indefinite periods of time.

We have created derivatives of *E. coli* with a primer methionine cycle similar to that in eukaryotic cells. The strains will allow for expression of N-formy-free polypeptides in *E. coli*.

Evolved microbial strains with unique genetic and metabolic imprints will serve as ancestors for the diversification of lines of industrially fit micro-organisms.

REFERENCES

Bogosian, G., et al., (1989) Biosynthesis and incorporation into protein of norleucine by *Escherichia coli* J. Biol. Chem. 264:531-539.

Clogston, C. L., Hsu, Y. R., Boone. T. C. and Lu, H. S.: Detection and quantitation of recombinant granulocyte colony-stimulating factor charge isoforms: comparative analysis by cationic-exchange chromatography, isoelectric focusing gel electrophoresis, and peptide mapping. Anal. Biochem. 202 (1992) 375-383.

Dong, M. S. Guo, Z., Philips, D. R., Bell, L. C., Howard, E., Blair, I. A., Gillam, E. M. J., Baba, T., Waerman, M. R. and Guengen, F. P.: Retention of N-formylmethionine in recombinant bacterial cytochrome P450 enzymes containing the N-terminal sequence MALLLAVFL. FASEB J. 9 (1995) A1486.

Guillon, J. M. Mechulam, Y., Schmnitter, J. M., Blanquet, S. and Fayat, G.: Disruption of the gene for Met-tRNA-fMet formyltransferase severely impairs growth of *Escherichia coli*. J. Bacteriol. 174 (1992) 42944301.

Hauschild-Rogat, P.: N-formylmethionine as a N-terminal group of *E. coli* ribosomal protein. Mol. Gen. Genet. 102 (1968) 95-101.

Hogset, A., Blingsmo, O. R. Gautvik, V. T., Saether, O., Jacobsen. P. B., Gordeladzo, J. O., Alestrom, P. and Gautvik, K. M. Expression of Human Parathyroid Hormone In *Escherichia Coli*. Biochemical and Biophysical Research Commnunications 166:1 (1990) 50-60.

Honda, S., Asano, T., Kajio, T., and Nishimura, O. *Escherichia coli*-Derived Human Interferon-gamma. with Cys-Tyr-Cys at the N-Terminus is Partially N.sup..alpha.-Acylated. Archives of Biochemistry and Biophysics 269 (1989) 612-622.

Marasco, W. A., Phan, S. H., Krutzsch, H., Showell, H. J., Feltner, D. E., Nairn, R., Becker, E. L. and Ward, P. A.: Purification and identification of formyl-methionyl-leucyl-phenylalanine as the major peptide neutrophil chemotactic factor produced by *Escherichia coli*. J. Biol. Chem. 259 (19S4) 5430-5439.

Mazel, D., Pochet, S. and Marliere, P.: Genetic characterization of polypeptide deformylase, a distinctive enzyme of eubacterial translation. EMBO J. 13 (1994) 914-923.

Milligan, D. L. and Koshland, Jr., D. E.: The amino terminus of the aspartate chemoreceptor is formylmethionine. J. Biol. Chem. 265 (1990) 4455-4460.

Rabbani, S. A., Yasuda T., Bennett H. P. J., Sung, W. L. Zahab, D. M., Tam, C. S. Goltman, D., and Hendy, G. N. Recobminant Human Parathyroid Hormone Synthesized in *Escherichia coli*. Journal of Biological Chemistry 263:3 (1988) 1307-1313.

Rose, K., Regamey, P., Anderegg, R., Wells, T., Proudfoot. A., Human interleukin-5 expressed in *Escherichia coli* has N-terminal modifications. Biochem J. 286 (1992) 825-828.

Sandman, K., Grayling, R. A., and Reeve, J. N. Improved N-terminal Processing of Recombinant Proteins Synthesized in *Escherichia coli*. Biotechnology 13 (1995) 504-506.

Specht, B., Oudenampsen-Kruger, E., Ingendoh. A., Hillenkamp, F., Lezius, A. G. and Spener, F.: N-terminal variants of fatty acid-binding protein from bovine heart overexpressed in *Escherichia coli*. J. Biotechnol. 33 (1994) 959-269.

Sugimoto, S., Yamaguchi. K. and Yokoo, Y.: Isolation and characterization of recombinant eel growth hormone expressed in *Escherichia coli*. J. Chromatog. 515 (1990) 483-494.

The invention claimed is:

1. A method for generating stable bacterial strains for producing non-formylated polypeptides comprising:
    a) inactivating a fmt gene coding for Met-tRNAi transformylase in the genome of at least one microbial clone to yield an altered clone,
    b) cultivating a population of microbial cells originating from the altered clone obtained in step a) under permanent proliferation in suspension allowing selection for a higher and stable proliferation rate;
    c) isolating descendant clones within the cultivated population of step b) still bearing the inactivation of step a).

2. A method according to claim 1, wherein step c) comprises isolating descendant clones within the cultivated population of step b) on the basis of increased proliferation rate, said clones having enhanced metabolic activities compared to the microbial clones of step a) while still bearing the alteration of step a).

3. A method according to claim 1, wherein the rate of proliferation of bacteria in step c) is significantly increased compared to bacteria of step a).

4. A method according claim 1, wherein the rate of proliferation of bacteria in step c) is comparable to the rate of proliferation of the natural bacteria.

5. A method according to claim 1, wherein bacteria of step c) have acquired a succession of mutations in the genome which stabilized the proliferation rate of the bacteria.

6. A method according to claim 5, wherein the mutations render the bacteria capable of competing with wild type bacteria.

7. A method according to claim 5, wherein the mutations are genetically stable.

8. A method according to claim 5, wherein the bacteria cannot genetically revert to wildtype bacteria.

9. A method according to claim 5, wherein the successive mutations acquired by the bacteria constitute tags that are genetically stable.

10. A method according to claim 1, wherein step c) is performed in minimal medium at 37° C.

11. A method according to claim 1, wherein step a) comprises the deletion of the entire def-first operon.

12. A method according to claim 1, wherein the bacteria is *E. coli*.

13. A method according to claim 1, wherein the bacteria of step c) is devoid of N-formylating activities.

14. A method according to claim 1, wherein steps b) and c) are performed with a device comprising:
 a) at least a first and at least a second culture vessel for receiving a culture;
 b) a gas source;
 c) a medium source;
 d) a source for a sterilizing agent; and
 e) a conduit system with means for selectively connecting one of said two culture vessels with said medium source as well as said two culture vessels with each other and for selectively connecting said respective other culture vessel with said source for said sterilizing agent.

15. A method according to claim 1, wherein the bacteria isolated in step c) is further transformed with a vector comprising a coding sequence for a peptide or protein of interest.

* * * * *